United States Patent [19]

Ueda

[11] 4,200,259
[45] Apr. 29, 1980

[54] PRESSURE RELIEF VALVE FOR BLOOD PRESSURE MEASURING INSTRUMENT

[75] Inventor: Kazuo Ueda, Tokyo, Japan
[73] Assignee: Ueda Works Co., Ltd., Tokyo, Japan
[21] Appl. No.: 909,568
[22] Filed: May 25, 1978
[30] Foreign Application Priority Data Jun. 27, 1977 [JP] Japan .............................. 52-99353[U]

[51] Int. Cl.$^2$ .......................... F16K 1/52; A61B 5/02
[52] U.S. Cl. .................... 251/285; 251/321; 128/685
[58] Field of Search ................. 251/321, 285; 128/2.05 G

[56] References Cited
U.S. PATENT DOCUMENTS

| | | | |
|---|---|---|---|
| 1,848,261 | 3/1932 | McIntyre | 251/321 |
| 2,960,304 | 11/1960 | Goss | 251/321 X |
| 3,823,707 | 7/1974 | Hayes | 251/285 X |
| 4,072,171 | 2/1978 | Narazawa | 128/2.05 G |

*Primary Examiner*—Arnold Rosenthal
*Attorney, Agent, or Firm*—Kane, Dalsimer, Kane, Sullivan & Kurucz

[57] ABSTRACT

A pressure relief valve for a blood pressure measuring instrument which is provided with a discharge mechanism for selectively discharging a small or large amount of compressed air. The discharge mechanism of simple structure is constituted from a small number of members including a valve member, a spring, an adjustment screw plug and a push button. A cuff pressure is automatically reduced at the predetermined reducing rate by rotating the adjustment screw plug during the measurement of blood pressure. Pushing of the push button also makes it possible to discharge at once the remaining cuff pressure after the measurement of blood pressure.

5 Claims, 3 Drawing Figures

PRESSURE RELIEF VALVE FOR BLOOD PRESSURE MEASURING INSTRUMENT

FIELD OF THE INVENTION

The present invention relates to an improved cuff pressure relief valve for blood pressure measuring instrument of the type, in which the highest and lowest blood pressure are measured by way of gradually reducing air pressure in a rubber bulb to detect appearing and disappearing of blood vessel noise in the course of the said pressure reducing, after pressurizing air in the cuff wrapped round an operator by means of the rubber bulb repeatedly manually grasped and depressed.

DESCRIPTION OF THE PRIOR ART

Generally there is specified a cuff pressure reducing rate. Usually 2 to 4 mHg/pulse is preferred as an ideal range of cuff pressure reducing rate during blood pressure measuring. It has been hitherto pointed out that an average man (particularly old man, high blood pressure patient) can't operate easily any prior art of blood pressure measuring instrument by way of continuous valve controlling at his home without any assistance by other person or in the absence of doctor.

SUMMARY OF THE INVENTION

The present invention is proposed to eliminate the drawbacks with the hitherto known blood pressure measuring instrument as mentioned above. In accordance with the present invention there is provided a pressure relief valve for blood pressure measuring instrument, in which the most preferable cuff pressure reducing rate is ensured only by releasing the rubber bulb, after pressurized air in the cuff to the predetermined height of pressure and further quick cuff pressure relieving is effected by way of push button operation after completion of blood pressure measuring. The pressure relief valve according to the present invention includes a single plug shaped valve member and a single push button to actuate the same, which are operative for a discharge mechanism. Owing to the arrangement as described above, the pressure relief valve is constructed in a more simple way.

It is a principal object of the present invention to provide a pressure relief valve for blood pressure measuring instrument, in which fine and quick pressure relieving is carried out with a single valve arrangement without any additional adjustment thereon in the course of blood pressure measuring.

It is a further object of the present invention to provide a pressure relief valve for blood pressure measuring instrument, which is simple in the structure and very inexpensive to be manufactured.

It is a further object of the present invention to provide a pressure relief valve for blood pressure measuring instrument, which is very easy to be operated by any average man, particularly old man, high blood pressure patient etc.

Other objects and advantageous features of the invention will be apparent from the description and claims.

BRIEF DESCRIPTION OF THE DRAWINGS

The nature and characteristic features of the invention will be more readily understood from the following description taken in connection with the accompanying drawings forming a part thereof; in which.

DESCRIPTION OF THE PREFERRED EMBODIMENT

Figure 1:
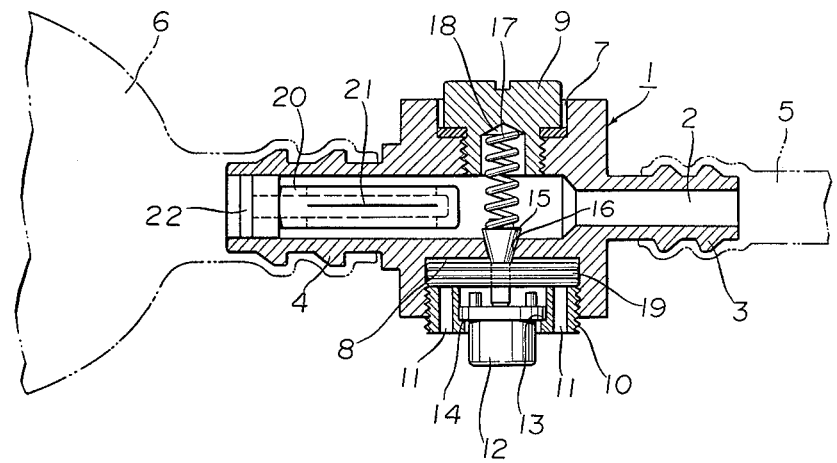
FIG. 1 is a vertically sectioned view of the pressure relief valve in accordance with the present invention.
Figure 2:
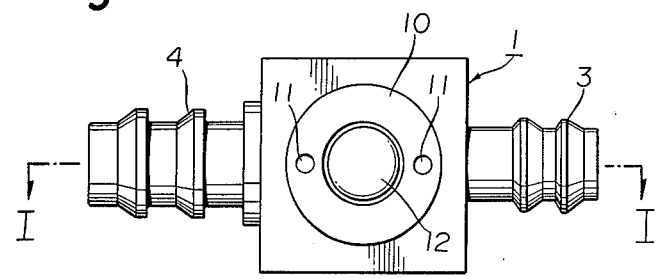
FIG. 2 is a plan view of the pressure relief valve as shown in FIG. 1.
Figure 3:
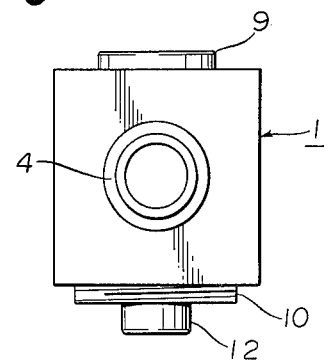
FIG. 3 is a front view of the pressure relief valve of FIG. 1.

As shown in FIG. 1, the reference numeral 1 denotes a square block shaped valve housing, which is provided with mushroom shaped connectors 3 and 4 at its front and rear ends respectively. The said connector 3 is connected to the rear end of a rubber tube 5 which is in communication with a cuff (not shown), while the said connector is connected to the front end of a rubber bulb 6. On the upper and lower portions of the housing 1 are formed circular recesses 7 and 8 respectively, the said circular recess 7 being adapted to receive therein the head of a cap shaped screw plug 9 to be screwed in the valve housing 1, while the said circular recess 8 being adapted to receive therein an adjustment screw plug in such a manner that it is freely rotated. The reference numeral 11 denotes two exhaust holes located symmetrically on the both sides of the center axis of the screw plug 10. The screw cap 9 and screw plug 10 are disposed to cross an air passage 2 of the valve housing at a substantially right angle. The reference numeral 12 denotes a push button which is arranged vertically displaceablly along the center axis of the said screw plug 10. The push button 12 is supported in the hollow space of the screw plug 10 by way of engagement of the upper surface of the stepped portion 13 of the same to the lower surface of the stepped portion 14 of the push button 12, wherein the head thereof is protruded outside the screw plug 10. The reference numeral 15 denotes a plug shaped valve member which is disposed in the valve housing at a substantially right angle to the air passage 2. The valve seat of the said valve member 15 is formed by an outwardly converging taper hole 16 itself, which has a through opening for serving to communicate the air passage in the valve housing with the outside atmosphere, while the head of the valve member is protruded into the outside of the valve housing (i.e. within the said recess 8) to come in contact with the backside of the push button. The reference numeral 17 denotes a valve closing spring which is arranged to be spanned between the bottom of circular recess 18 of the screw cap 9 and the upper surface of the valve member 15. Further the reference numeral 19 denotes a stopping spring which is also inserted between the adjustment plug 10 and the bottom surface of the said circular recess 8. Owing to the arrangement of the said resilient means 19, the adjustment plug can be kept fixed in the screw engagement position. It is to be noted that as the adjustment plug is further screwed in to open the valve member, the resilient force of the spring 17 acts increasingly on the upper surface of the adjustment plug and the screw engagement of the both members 1 and 10, resulting in increased screw engagement and immovability therebetween. The reference numeral 20 denotes a well known check valve of rubber material disposed in the air passage 2, the reference numeral 21 does slits formed on the side wall of the said check valve 20 and the reference numeral 22 does a filter.

Now the pressure regulating and relieving valve in accordance with the present invention is adjusted in the following manner; The adjustment plug 10 is screwed in or out with the aid of a spanner which is specially designed for this valve of the invention to fit into the exhaust holes 11, so as to ensure the required opening of the valve member 15 so that the cuff pressure is decreased at the specified rate during measuring. Once the said valve opening is predetermined, no additional adjustment is required. An operator can always lower the cuff pressure at the specified rate of pressure reducing only by releasing the rubber bulb, after increasing the cuff pressure to the required height by way of depressing the rubber bulb, while he can exactly measure the highest and lowest blood pressure. As the stopping spring 19 acts always against the adjustment plug in the downward direction, the said adjustment plug is remained fixed with the push button held thereon during measuring. After measuring, quick release of the residual cuff pressure is carried out only by depressing the push button with the use of his finger, while he is grasping the rubber bulb. It will be obvious that pressurized air in the passage 2 is discharged through the tapered hole 16 and the clearance between the inner wall of the recess 8 and the adjustment plug 10 and through the exhaust holes 11.

As described above, present invention lies in that the pressure relief valve comprizes a single plug shaped valve member and a single push button in such a simple construction that has never been hitherto achieved, causing the cuff pressure to be automatically reduced at the specified pressure reducing rate without any valve operation during measuring and moreover the resultant cuff pressure to be released by way of valve operation using a push button. It, therefore can be concluded that the present invention has brought about a remarkable improvement with such kind of pressure relief valve.

It should, of course, be understood that the description and drawings herein are illustrative merely and a variety of modifications and changes can be made in the structure as disclosed above without any departure from the spirit of the invention.

What is claimed is:

1. A pressure relief valve for a blood pressure measuring instrument comprising a valve housing having a hollow space forming an air passage, a discharge mechanism on the housing for selectively discharging a small or large amount of compressed air through the air passage, the discharge mechanism including a valve seat consisting of an outwardly converging tapered hole providing communication between the air passage in the valve housing and the outside thereof, a valve member shiftable between a position in contact with the valve seat and a position apart therefrom, a head portion of the valve member protruding above a lower surface of said valve housing, a valve closing spring interposed between an upper surface forming a hollow space in the valve housing and the valve member, a recess formed in the valve housing, an adjustment screw plug threadedly interengaged with the recess and having exhaust holes formed therein, a push button disposed in the adjustment screw plug in a manner that the push button is permitted to move upward and downward for a restricted distance and can open or close the valve member in cooperation with the spring in contact with the head portion of the valve member, the adjustment screw plug being rotatable to push the push button downwardly thereby making it possible to automatically discharge small amounts of compressed air at the decrease during the measurement of blood pressure, and direct pushing of the push button causing the remaining cuff pressure to quickly discharge after the measurement of blood pressure.

2. Pressure relief valve for blood pressure measuring instrument as set forth in claim 1, wherein the valve closing spring is spanned between the upper portion of said hollow space of the valve housing and the valve member.

3. Pressure relief valve for blood pressure measuring instrument as set forth in claim 1, wherein the exhaust holes in the adjustment screw plug are located symmetrically on both sides of the center axis of the said adjustment screw plug, and as the valve member is displaced in a valve opening position, pressurized air in the air passage is discharged through the taper hole 16 and then the clearance formed between the bottom surface of the recessed portion 8 of the valve housing and the said adjustment screw plug.

4. Pressure relief valve for blood pressure measuring instrument as set forth in claim 1, wherein the push button suporting portion of the said adjustment screw plug is provided with a stepped portion in the hollow space thereof, the upper surface of the said stepped portion 13 being in engagement with the lower surface of the stepped portion 14 of the push button, which is supported displaceablly in the hollow space of the adjustment screw plug along the center axis thereof in such a manner that the head portion of the siad push button is protruded outside the valve housing.

5. Pressure relief valve for blood pressure measuring instrument as set forth in claim 1, wherein a stopping spring 19 is inserted between the adjustment screw plug and the bottom surface of the circular recess, the spring force of the said spring 19 causing the said adjustment screw plug to be maintained fixed in the screwed-in position.

* * * * *